United States Patent [19]

Kauffman

[11] 4,085,268
[45] Apr. 18, 1978

[54] DISUBSTITUTED S-TRIAZINES

[75] Inventor: William J. Kauffman, Manheim, Pa.

[73] Assignee: Armstrong Cork Company, Lancaster, Pa.

[21] Appl. No.: 711,472

[22] Filed: Aug. 4, 1976

[51] Int. Cl.$^2$ .......................................... C07D 251/34
[52] U.S. Cl. ................................................. 544/221
[58] Field of Search ................... 260/248 NS; 544/221

[56] References Cited

U.S. PATENT DOCUMENTS 2,580,468  1/1952  Schaefer et al. ............. 260/248 NS
3,682,909  8/1972  Hagemann .................. 260/248 NS Primary Examiner—John M. Ford

[57] ABSTRACT

Disubstituted s-triazines are prepared by the reaction of allophanoyl chlorides with a metal cyanate in the presence of a dipolar aprotic solvent. The products may be used as intermediates in the production of pharmaceuticals, insecticides, disinfectants and in the preparation of polymers.

3 Claims, No Drawings

DISUBSTITUTED S-TRIAZINES

BACKGROUND OF THE INVENTION

1. Field of the Invention

This invention relates to a process for the production of disubstituted s-triazines. It also relates to the compounds obtained from such process, some of which are novel themselves.

2. Description of the Prior Art

The synthesis of s-triazine derivatives of the isocyanurate type has hereto been reported. In U.S. Pat. No. 3,684,807, unsymmetrical, trisubstituted isocyanurates are prepared by the reaction of the metal cyanate, an organic isocyanate and an organic halide in the presence of a dipolar aprotic solvent. While this process is superior to those processes described, for example, in *Journal of Organic Chemistry*, 26, page 3334 (1961) and *The Journal of the American Chemical Society*, 82, page 6858 (1965), giving extremely good yields of isocyanurate, many of the reactions take extremely long times, e.g. up to 64 hours. Further, this synthetic route can only be used for preparation of compounds of the triazine type having substitutents on each one of the nitrogen atoms.

There have been a variety of techniques useful for the preparation of disubstituted s-triazine materials. For example, one of the most convenient syntheses of the pharmacologically active disubstituted isocyanurates of the formula

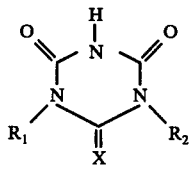

where X is oxygen or sulphur and $R_1$ and $R_2$, which may be the same or different, each represent hydrogen, or optionally substituted aliphatic, cycloaliphatic, araliphatic, aromatic or heterocyclic radical have largely been confined to the reaction of ureas or thioureas with N-chlorocarbonyl isocyanate. While this process provides compounds of good pharmacological activity, commercial and even laboratory preparations using such route are hazardous due to the high toxicity of the reactants.

SUMMARY OF THE INVENTION

It is one object of the present invention to prepare disubstituted s-triazines.

It is an additional object of this invention to prepare unsymmetrically disubstituted s-triazines by a route that uses relatively non-toxic reactants.

This and other objects of the present invention can be effected by the reaction of allophanoyl chlorides with metal cyanates in a dipolar aprotic solvent. Such a reaction route provides compounds that have heretofore been unavailable.

DESCRIPTION OF THE PREFERRED EMBODIMENTS

The overall reaction of this invention may be summarized as follows:

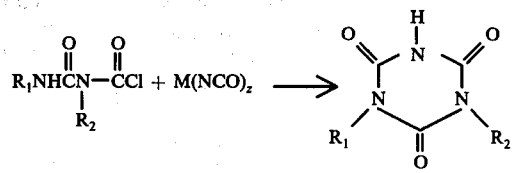

where $R_1$ and $R_2$ may be the same or different and each represent hydrogen or substituted or unsubstituted aliphatic, cycloaliphatic, araliphatic, aromatic or heterocyclic radical, and Z represents the valence of the metal M, which is an alkali metal, an alkali earth metal, or silver, with the proviso that $R_1$ and $R_2$ are not the same when aromatic and/or heterocyclic. The reaction yield is disadvantageously affected when a totally aromatic urea or thiourea is used in the overall reaction disclosed above. The allophanoyl chloride having the substituents $R_1$ and $R_2$ can be prepared by any of the well-known reaction routes. Especially preferred for the preparation of these compounds are the reaction of N,N'-disubstituted ureas with phosgene or thiophosgene as follows:

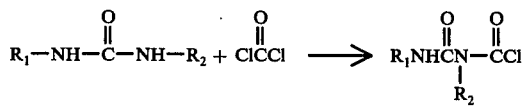

where $R_1$ and $R_2$ are as hereinbefore described. This reaction has generally been described in U.S. Pat. No. 3,337,621 and is typically carried out by the reaction of N,N'-disubstituted ureas with phosgene. By the term N,N'-disubstituted urea as used herein is meant a urea having the characteristic group —NHCONH—, with each nitrogen atom thereof having attached thereto a hydrogen atom and an aliphatic, cycloaliphatic, araliphatic, aromatic or heterocyclic radical free of groups which are reactive with phosgene.

Preferably, $R_1$ or $R_2$ of the ureas as prepared by the above-disclosed synthetic route, may be the same of different aliphatic or substituted aliphatic radicals and include linear, as well as branched alkyl, radicals of from 1 to 18 carbon atoms. Preferably, such radicals may be 1 to 8 carbon atoms, most preferably 1 to 4 carbon atoms. In some cases, when $R_1$ or $R_2$ is aliphatic or branched aliphatic, such may contain at least one double or triple bond. In such cases, $R_1$ or $R_2$ are preferably alkenyl with 1 to 8 carbon atoms.

Suitable cycloaliphatic radicals for $R_1$ and/or $R_2$ have from 5 to 12 and preferably have 5 to 8 carbon atoms in the ring system.

As optional substituents on the aliphatic, branched aliphatic or cycloaliphatic radical are included lower O-alkyl and S-alkyl radicals having preferably from 1 to 4 carbon atoms. Halogen, preferably fluorine or bromine, or cyano radicals and, on the cycloaliphatic radicals, lower alkyl groups of from 1 to 4 carbon atoms are also included as optional substituents.

$R_1$ and/or $R_2$ may also be araliphatic radicals containing from 1 to 4 and preferably from 1 to 2 carbon atoms in the alkyl portion, and naphthyl or preferably phenyl radical in the aromatic portion.

As aromatic radicals for $R_1$ or $R_2$ are included those from 6 to 14 carbon atoms in the ring system, the naphthyl radical and especially the phenyl radical being the preferred aromatic radicals.

As heterocyclic radicals for $R_1$ or $R_2$ are those which contain 5, 6, or 7 ring members; with oxygen or sulphur atom, or a nitrogen atom substituted by a lower alkyl radical, preferably from 1 to 4 carbon atoms. The hetero ring system may optionally be fused to a benzene ring, which optionally may also be partially hydrogenated.

In addition to the substituents already mentioned in respect to the aliphatic radicals, suitable substituents on the araliphatic, aromatic or heterocyclic ring system include nitro groups and $C_1$ to $C_4$ haloalkyl groups, preferably fluoroalkyl or chloroalkyl. Trifluoromethyl radical is mentioned by way of example as a preferred halogen alkyl radical.

Using substantially equimolar amounts of the N,N'-disubstituted urea and of the phosgene, the reaction proceeds smoothly with almost quantitative yields of the corresponding N,N'-disubstituted allophanyl chloride. Hydrogen chloride is evolved, indicating that the reaction is taking place. An excess of phosgene can be used if desired, but no matter how much the excess employed, it does not react with the hydrogen atom of the characteristic allophanyl chloride group,

The reaction is best carried out in the presence of an inert solvent for the N,N'-disubstituted urea, of which benzene is preferred.

The aforementioned ureas used as intermediates to prepare the unsymmetrically disubstituted s-triazine derivatives in accordance with the present invention are all known and can be obtained by known processes. As a particularly useful process for obtaining such intermediate ureas and thioureas are the reactions of isocyanates and isothiocyanates with primary amines according to the following equation

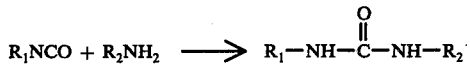

where $R_1$ and $R_2$ are as hereinbefore described. As a general route for the syntheses of ureas of this type, a preferred method is described in Saunders, J.S. *Polyurethanes*, Chemistry and Technology, Part I, page 176. The reaction takes place conveniently by the addition of the isocyanate with the corresponding amine in a non-reactive organic solvent, with or without the addition of a catalytic reagent.

The following radicals are particularly useful when bonded to the isocyanate group, such being used in the aforesaid reaction with primary amines: p-trifluoromethylphenyl; p-nitrophenyl; methyl; carbethoxymethyl; ethyl; isopropyl; normal propyl; t-butyl; isobutyl; n-butyl; cyclopentyl; cyclohexyl; 2-ethylhexyl; dodecyl; tetradecyl; hexadecyl; phenyl; cyclopentadienyl; propynyl; B-chloroethyl; B-naphthyl; benzyl; stearyl; B-cyanoethyl; 4-methoxynaphthobenzyl; tolyl; xylyl; p-nitrophenyl; p-chlorophenyl; p-methoxyphenyl; p-ethoxyphenyl; diphenyl; diphenyl urethane; nitronaphthyl; nitrobenzyl; carbethoxymethyl; and the like.

Primary amines particularly useful as reactants with the aforementioned isocyanates to yield the respective ureas may include methylamine; ethylamine; octylamine; stearylamine; B-bromoethylamine; 1-cyano-1-phenylethylamine, 1-cyano-1-methylethylamine; glycine ethyl ester; 2-amino-1-methyl-cyclohexane; hexahydrobenzylamine; 2-aminotoluene, 3-chloro-2-aminotoluene; 4-chloro-2-aminotoluene; 5-nitro-4-amino-1,3-dimethyl benzene; 6-nitro-4-amino-1,3-dimethyl benzene; 5-amino-1,3-dimethylbenzene; 5-amino-1,3-bis-trifluoromethyl benzene; 2-amino-1,4-dimethyl benzene; 2-amino-1-methyl-3-ethyl benzene; 6-amino-1,2,4-trimethyl benzene; 2-amino-1,3,5-trimethyl benzene; 2-amino-1,3-diethyl benzene; 4-amino-1,3-dimethyl-5-ethyl benzene; 4-amino-1-methyl-3,5-diethyl benzene; 2-amino-1,3,-diisopropyl benzene; 5,6,7,8-tetrahydro-2-naphthylamine; 5-chloro-2-aminobenzotrifluoride; 6-chloro-2-aminotoluene; 4,5-dichloro-2-aminotoluene; 3-nitro-2-aminotoluene; 4-nitro-2-aminotoluene; 5-nitro-2-aminotoluene; 6-nitro-2-aminotoluene; 4-chloro-5-nitro-2-aminotoluene; 3-aminotoluene; 4-chloro-3-aminotoluene; 6-chloro-3-aminotoluene; 4,6-dichloro-3-aminotoluene; 4-aminotoluene; 2-chloro-4-aminotoluene; 2-nitro-4-aminotoluene; 3-nitro-4-aminotoluene; 2-amino-1-ethylbenzene; 1-amino-1-phenylethane; 2,3-dimethyl aniline; 3,4-dimethyl aniline; 2,6-dimethyl aniline; and 2,4-dimethyl aniline; 5-chloro-2-aminotoluene; 4-chloro-3-aminobenzotrifluoride; 1-amino-2-phenylethane; 2-amino-1-isopropylbenzene; 5-amino-1,2,4-trimethyl benzene; 5,6,7,8-tetrahydronaphthyl-1-amine; 1-aminonaphthylene; 2-chloro-4-nitroaniline; 2-chloroaniline; 3-nitroaniline; 3,5-dichloroaniline; 2,4,5-trichloroaniline; 2,4-dichloroaniline; 2,3-dichloroaniline; 2,5-dichloroaniline; 3-chloroaniline; 4-chloroaniline; 4-chloro-2-nitroaniline; aniline; 2-nitroaniline; 4-nitroaniline; 5-chloro-2-nitroaniline; 4-chloro-3-nitroaniline; 3-chloro-4-nitroaniline; 4,6-dichloro-2-nitroaniline; 2,5-dichloro-4-nitroaniline; 2,6-dichloro-4-nitroaniline; 2-aminopyridine; 2-aminothiazole; 2-aminobenzthiazole; and the like.

The allophanoyl chlorides produced from the above-disclosed reactants and reactions are further reacted with metal cyanates to form the unsymmetrically disubstituted s-triazines in accordance with the present invention. These cyanates comprise the alkali, alkali earth metal or silver cyanates. As examples of such compounds are sodium cyanate, potassium cyanate, lithium cyanate, rubidium cyanate, caesium cyanate, calcium cyanate, barium cyanate, strontium cyanate, magnesium cyanate, beryllium cyanate, and silver cyanate.

As indicated, the reaction between the allophanoyl chloride and the metal cyanates is carried out in the presence of a dipolar aprotic solvent. These solvents have utility as solvent media in accordance with this invention in that they are liquid under the conditions of the reaction; they have a high dielectric constant, i.e. greater than about 15° at 25° C.; they are dipolar in character, i.e. one part of their molecule has a more positive electrical charge relative to other parts of the molecule resulting in a molecular dipolar structure; they are sufficiently inert so as not to enter into and change dileteriously the course of the reaction; and they exert a good solvent effect on either or both of the reactant species. A mixture of solvents satisfying the foregoing criteria can, of course, be employed. Such aprotic dipolar solvents useful for carrying out the method of this invention are the alkyl pyrrolidones such as N-methyl pyrrolidone-2 and N-ethyl pyrrolidone-2; sulfoxides such as dimethylsulfoxide and diethylsulfoxide; alkyl amides including N,N-dimethylformamide, N,N-diethylformamide, N,N-dimethylacetamide, and N,N-diethylacetamide; alkyl phosphoramides and aryl phosphoramides such as hexamethylphosphoramide, hexaethylphosphoramide and hexaphenylphosphoramide; nitriles such as acetonitrile and benzonitrile and alkyl ureas such as tetramethyl urea and tetraethyl urea. Compatible mixtures of the aforementioned diprotic apolar solvent may also be used herein.

The temperatures utilized in forming the disubstituted s-triazine derivatives in accordance with the practice of the present invention can range from as low as 0° and can be as high as 200° C. In most instances, however, it is preferred to use temperatures in the range of about 25° to 100° C. Depending upon the temperature employed and the reactivity of the allophanoyl chloride used, the time required to carry out the method of this invention may vary from about 0.5 to about 8 hours.

The mole ratio of the metal cyanate to the allophanoyl chloride or thioallophanoyl chloride is preferably from about 1:1 to about 10:1 and more preferably from about 1:1 to about 5:1, and most preferably from about 1:1 to about 2:1. Any mole ratio above 10:1 does not noticeably contribute to the yield of the disubstituted s-triazine derivative.

While pressure is not narrowly critical and may be from below one atmosphere to over 10,000 psig, in most cases, the reaction is preferably conducted at atmospheric pressure.

The following examples are illustrative of the preferred embodiments of this invention, but are not meant to limit it in any way. A variety of modifications and variations will become obvious to those skilled in the art upon a reading of the present application, and all such obvious variations and modifications are to be taken as being within the scope of the claims appended hereto.

EXAMPLE 1

1-phenyl-3-allyl urea

A solution of 100 g (0.84 mole) phenylisocyanate in 50 ml of benzene was added dropwise over a period of 30 minutes to a stirring solution of 60 g (1.05 mole) allyl amine in 2 liters of benzene. The mixture was stirred overnight and suction filtered yielding 120 g (95% yield) of 1-phenyl-3-allyl urea with a melting point of 112°–113°. This material was also characterized by IR and nmr analysis.

EXAMPLE 2

5-phenyl-3-allyl allophanoyl chloride

Fifteen ml of phosgene was condensed in a graduated trap using a dry ice acetone bath. The ice bath was removed, and with the assistance of a slow flow of dry nitrogen, passed into a cold (10° C.) mixture of 17.6 g (0.1 mole) 1-phenyl-3-allyl urea and 250 ml of benzene (dry) over a period of one hour. The mixture was then heated at 80° C. for 2 hours yielding a clear solution. Infrared (NH — 2.94 ;c═o, 5.74) and nmr analysis were consistent with the allophanoyl chloride structure.

To further confirm the structural assignments, biuret derivatives were prepared as outlined below. The above benzene solution was added dropwise to a stirred solution of 22 g (0.2 mole) of p-toluidine in 200 ml of dry ether over a period of 15 minutes. After one hour the precipitate was suction filtered and the filtrate concentrated on a rotary evaporator at reduced pressure. The initial precipitate was shown to be 13.4 g of p-toluidine hydrochloride (94% of theoretical) by IR and mixed melting point. The residue obtained after evaporation of the solvents was recrystallized from ethanol/water yielding 25.1 g (85% yield) of 1-phenyl-3-allyl-5-p-tolyl biuret; M.P. 80°–81° C.

Anal. Calcd. for $C_{18}H_{19}N_3O_2$: C, 69.88; H, 6.19; N, 13.58. Found: C, 70.03; H, 6.23; N, 13.55 Mol Wt. Calcd: 309, Found: 308.

To further clarify the position of the allyl group, another sample of the allophanoyl chloride was reacted with allylamine in analogous manner to produce the 1-phenyl-3,5-diallyl biuret. NMR analysis of this compound confirmed the location of the allyl substituent to be the #3 position in the previous biuret sample.

EXAMPLE 3

3-phenyl-5-allyl isocyanuric acid

A benzene solution of 5-phenyl-3-allyl allophanoyl chloride (0.1 mole) prepared as previously described was concentrated to 0.50 ml under reduced pressure. This solution was added dropwise to a stirring mixture of 16.0 g potassium cyanate (0.2 mole) and 300 ml of anhydrous DMF. The addition took 2 hours and the temperature was maintained at 0°–5° C. during the addition. The solution was warmed to room temperature and stirred an additional hour. The excess potassium cyanate was removed by filtration and the filtrate concentrated under reduced pressure on a rotary evaporator. The residue was treated with 200 ml of water and the water insolubles separated by filtration. Acidification of the water layer with concentrated HCl resulted in precipitation of a gummy mass. This mixture was extracted with 400 ml of methylene chloride and the methylene chloride layer separated, dried over anhydrous sodium sulfate and concentrated. Distillation of the crude product gave 18.0 g of 3-phenyl-5-allyl isocyanuric acid (75% yield); b.p. 185° C./0.01 mm, m.p. 63°–65°.

Anal. Calcd for $C_{12}H_{11}N_3O_3$: C, 58.77; H, 4.52; N, 17.13. Found: C, 58.89; H, 4.64; N, 17.39.

IR and NMR analysis was consistent with the assigned structure. A portion of this material was also alkylated with allyl chloride and triethylamine in DMF solvent and the product was identical with a known sample of 1-phenyl-3,5-diallyl isocyanate prepared by a different procedure.

EXAMPLE 4

3-phenyl-5-allyl isocyanuric acid

The conditions and reactants of Example 3 were repeated except the amount of potassium cyanate was increased to 24 g (0.3 mole). A yield of 73% 3-phenyl-5-allyl isocyanuric acid was obtained.

EXAMPLE 5

3-phenyl-5-butyl isocyanuric acid

A benzene solution (50 ml) of 5-phenyl-3-butyl allophanoyl chloride (0.1 mole) was prepared by reaction of phosgene with 1-phenyl-3-butyl urea by the method of Example 2. This solution was added dropwise to 16.0 g of potassium cyanate in 300 ml of anhydrous DMF as described in Example 3. After similar work-up, 17.0 g (70% yield) of 3-phenyl-5-butyl isocyanuric acid was obtained; b.p. 172° C./.01 mm, m.p. 54°–56° C. IR and NMR analysis were consistent with the assigned structure.

A portion of this material was alkylated with butylbromide and triethylamine in DMF solvent. An 80% yield of 1-phenyl-3,5-dibutyl isocyanurate was obtained; m.p. 58°–59°.

Anal. Calcd. for $C_{17}H_{23}N_3O_3$: C, 64.33; H, 7.30; N, 13.24. Found: C, 64.28; H, 7.52; N, 13.42.

This material was found to be identical to a known sample of 1-phenyl-3,5-dibutyl isocyanurate prepared by a different procedure.

EXAMPLE 6

3,5-dibutyl isocyanuric acid

A benzene solution (50 ml) of 5,3-dibutyl allophanoyl chloride (0.1 mole) was prepared by reaction of phosgene with 1,3-dibutyl urea by the method of Example 2. This material was reacted with 16.0 g (0.2 mole) of potassium cyanate as described above. After work-up, 9.3 g (38% yield) of dibutyl isocyanuric acid was obtained; m.p. 86°–88° C. IR and nmr analysis was consistent with the assigned structure.

What is claimed is:

1. A method of preparing disubstituted s-triazines comprising forming a reaction mixture of an allophanoyl chloride of the formula $R_1NHCON(R_2)COCl$ and an alkali, alkali earth metal or silver cyanate and reacting the said allophanoyl chloride with said cyanate in the presence of a dipolar aprotic solvent at a temperature sufficient to effect the formation essentially of an s-triazine corresponding to the formula

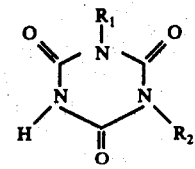

wherein $R_1$ and $R_2$ are the same or different and represent a member selected from the group of linear or branched alkyl having from 1 to 18 carbon atoms, linear or branched alkenyl having from 1 to 8 carbon atoms, cycloalkyl having from 5 to 8 carbon atoms in the ring system, phenyl alkyl having from 1 to 4 carbon atoms in the alkyl group, naphthyl alkyl having from 1 to 4 carbon atoms in the alkyl group, $C_6$ to $C_{14}$ and carbocyclic aryl with the proviso that $R_1$ and $R_2$ are not the same when aromatic.

2. The method of claim 1 wherein said cyanate is an alkali metal cyanate and the temperature is from 0° to 200° C.

3. The method of claim 1 wherein the temperature is from 25° to 100° C.

* * * * *